United States Patent [19]
Walker

[11] Patent Number: 5,609,639
[45] Date of Patent: *Mar. 11, 1997

[54] PROSTHESIS FOR KNEE REPLACEMENT

[76] Inventor: Peter S. Walker, The Institute of Orthopaedics. Dept. of Biomedical Engineering, Royal National Orthopaedic Hospital, Brockley Hill Stanmore, Middlesex, United Kingdom, HA7 4LP

[*] Notice: The term of this patent shall not extend beyond the expiration date of Pat. No. 5,330,533.

[21] Appl. No.: 163,623

[22] Filed: Dec. 9, 1993

Related U.S. Application Data

[63] Continuation-in-part of Ser. No. 829,369, Feb. 3, 1992, Pat. No. 5,330,533.

[30] Foreign Application Priority Data

Feb. 4, 1991 [GB] United Kingdom .................... 9102348
Jul. 16, 1993 [GB] United Kingdom .................... 9314839

[51] Int. Cl.⁶ ....................................................... A61F 2/38
[52] U.S. Cl. ........................................................... 623/20
[58] Field of Search ................................. 623/16, 18, 20

[56] References Cited

U.S. PATENT DOCUMENTS

| | | |
|---|---|---|
| 3,958,278 | 5/1976 | Lee et al. . |
| 4,085,466 | 4/1978 | Goodfellow et al. . |
| 4,215,439 | 8/1980 | Gold et al. . |
| 4,224,696 | 9/1980 | Murray et al. . |
| 4,285,070 | 8/1981 | Averill . |
| 4,340,978 | 7/1982 | Buechel et al. . |
| 4,353,136 | 10/1982 | Polyzoides et al. ........................ 623/20 |
| 4,586,933 | 5/1986 | Shoji et al. ................................. 623/20 |
| 4,673,407 | 6/1987 | Martin ........................................ 623/20 |
| 4,711,639 | 12/1987 | Grundei ..................................... 623/20 |
| 4,714,474 | 12/1987 | Brooks, Jr. et al. ....................... 623/20 |
| 4,728,332 | 3/1988 | Albreletsson ............................. 623/20 |
| 4,822,362 | 4/1989 | Walker et al. ............................. 623/20 |
| 4,822,365 | 4/1989 | Walker et al. ............................. 623/20 |
| 5,064,437 | 11/1991 | Stock et al. ................................ 623/20 |
| 5,071,438 | 12/1991 | Jones et al. ........................... 623/18 X |
| 5,080,675 | 1/1992 | Lawes et al. .............................. 623/20 |
| 5,116,375 | 5/1992 | Hofmann .................................. 623/20 |
| 5,133,758 | 7/1992 | Hollister ................................... 623/20 |
| 5,147,405 | 9/1992 | Van Zile et al. .......................... 623/20 |
| 5,171,283 | 12/1992 | Pappas et al. ............................. 623/20 |
| 5,219,362 | 6/1993 | Tuke et al. ................................. 623/20 |
| 5,282,868 | 2/1994 | Bahler ....................................... 623/20 |
| 5,387,240 | 2/1995 | Pottenger et al. ......................... 623/20 |
| 5,395,401 | 3/1995 | Bahler ....................................... 623/20 |

FOREIGN PATENT DOCUMENTS

| | | |
|---|---|---|
| 0021421 | 1/1981 | European Pat. Off. . |
| 0327297 | 8/1989 | European Pat. Off. . |
| 0349173 | 1/1990 | European Pat. Off. . |
| 0442330 | 8/1991 | European Pat. Off. . |
| 0498586A1 | 8/1992 | European Pat. Off. . |
| 0529408A1 | 3/1993 | European Pat. Off. . |
| 3529894 | 3/1987 | Germany . |
| 1534263 | 11/1978 | United Kingdom . |
| 1567007 | 5/1980 | United Kingdom . |
| 2061730 | 5/1981 | United Kingdom . |
| 2219942 | 12/1989 | United Kingdom . |
| WO92/03108 | 3/1992 | WIPO . |

*Primary Examiner*—Mary Beth Jones
*Attorney, Agent, or Firm*—Lowe, Price, LeBlanc & Becker

[57] ABSTRACT

A knee prosthesis includes a femoral component in which the condyles have a continuous contact surface for the tibial bearing surface and in which the sagittal radius is constant from posterior to a point more anterior than the distalmost point, The tibial bearing surface is shaped to have a curvature which corresponds closely with that of the femoral condylar surfaces. The tibial component includes a plastics meniscus component supported on a metal platform for sliding movement in the anterior-posterior direction and the mating surface between the meniscus and platform has a sagittal curvature which is larger than the sagittal radius of the femoral condyles.

18 Claims, 11 Drawing Sheets

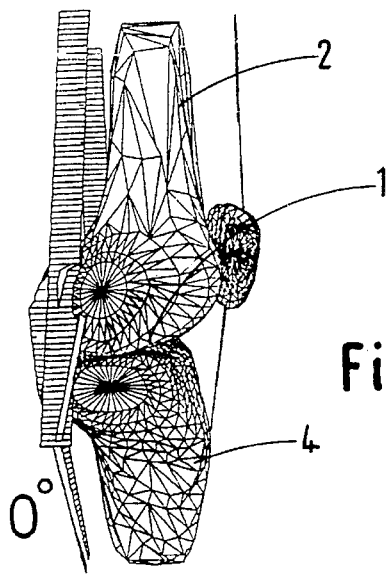
Fig.1(a) 0°
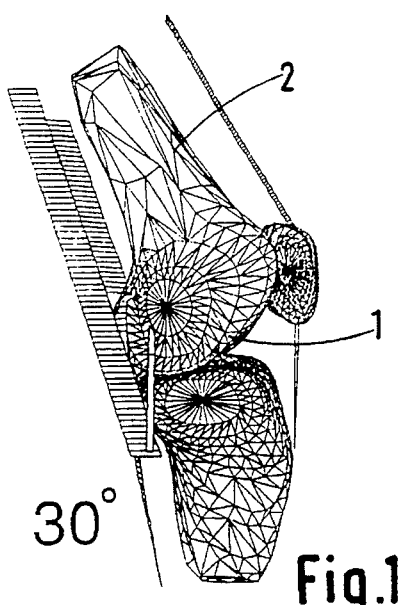
Fig.1(b) 30°
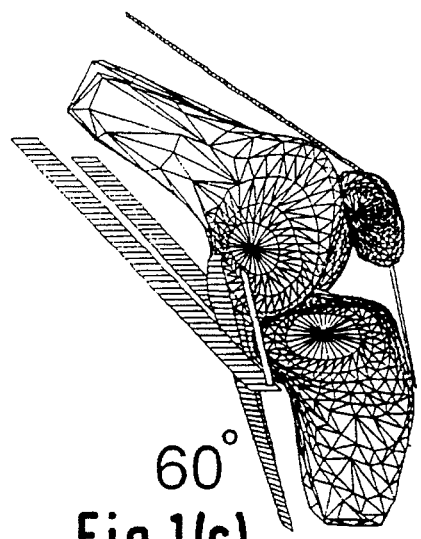
Fig.1(c) 60°
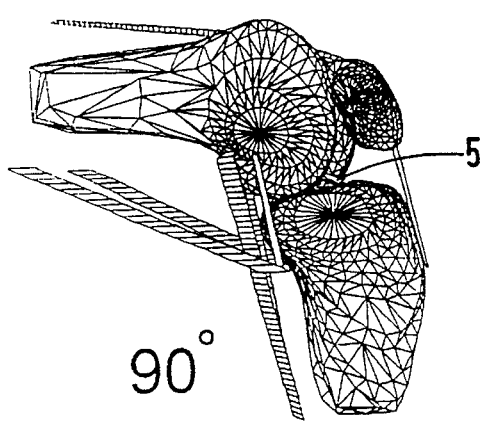
Fig.1(d) 90°
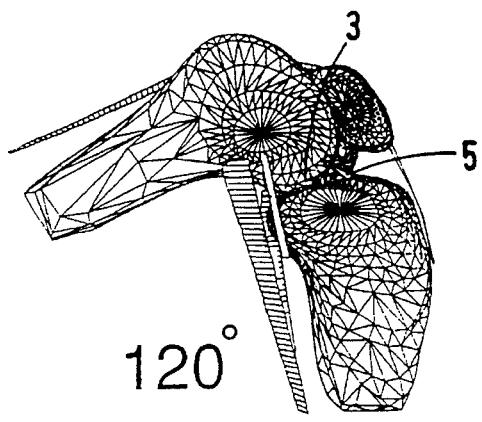
Fig.1(e) 120°

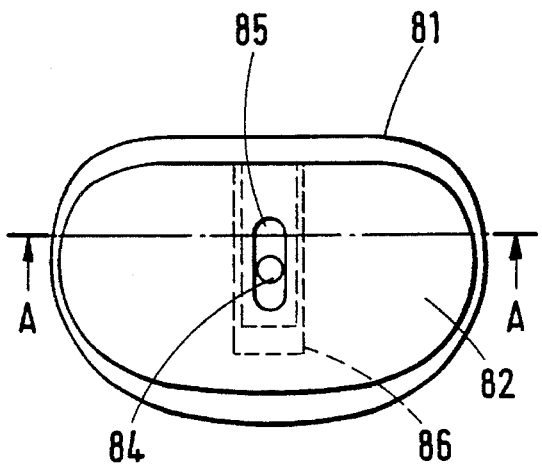
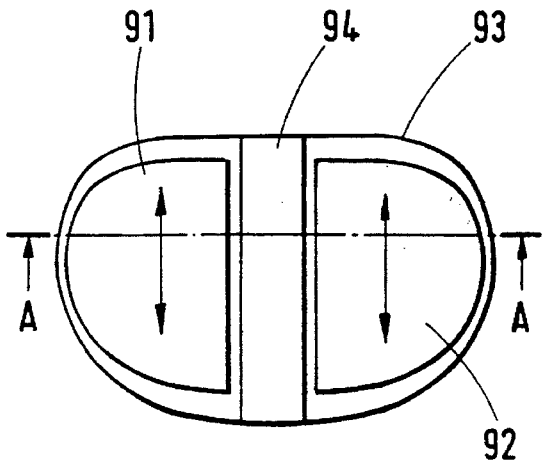
Fig.8(a)　　　　　Fig.9(a)
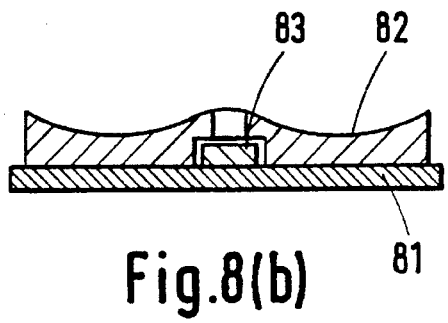
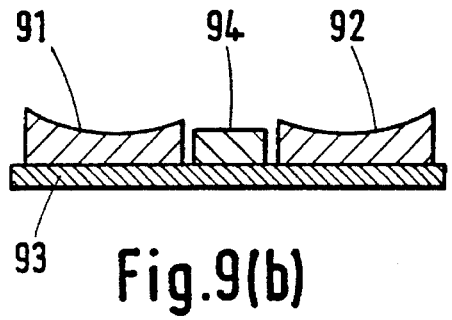
Fig.8(b)　　　　　Fig.9(b)
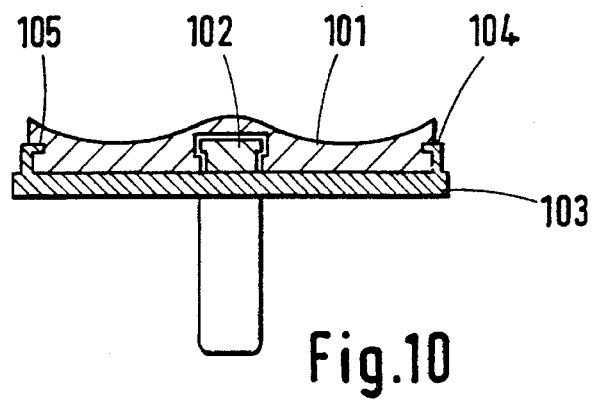
Fig.10

PROSTHESIS FOR KNEE REPLACEMENT

This invention is a continuation-in-part application of U.S. Ser. No. 07/829,369 filed on Feb. 3, 1992, now U.S. Pat No. 5,330,533.

BACKGROUND OF THE INVENTION

Most of the knee replacement designs in current use are of the Condylar Replacement type, where the arthritic joint surfaces are resected and are replaced with metal and plastic surfaces. There are two conflicting requirements in design; first, the desirability for freedom of motion requires relatively low conformity between the femoral and tibial surfaces, while the desirability for low contact stresses on the plastic surface requires high conformity. This conflict similarly applies to the patello-femoral bearing joint.

SUMMARY OF THE INVENTION

The present invention provides several approaches to a solution of this dilemma. First, it provides a femoral component which alters the sagittal radius and which has continuous contact surfaces for the tibial surface and also, preferably, with the patella surface. Secondly, the invention relates to a sliding bearing type of prosthesis where guide tracks for the tibial bearing surface are curved in the sagittal plane to provide the necessary stability, as well as freedom for translational motion in the anterior-posterior direction.

The above two broad concepts may be combined in a single prosthesis or employed individually depending on the requirements of a particular case. The invention also includes variations of the above concepts and various designs of tibial components.

Another problem in the design of a knee prosthesis is to provide for the proper degree of rotational freedom of motion, without at the same time leading to an unstable linkage or one which is insufficiently robust to withstand loadings and movement during walking. The invention is therefore also directed in another aspect to an artificial knee joint in which this problem is addressed.

According to one aspect of the invention there is provided a knee prosthesis which comprises:

(a) a femoral component having a pair of condylar bearing surfaces;

(b) a tibial component including a tibial platform;

(c) a meniscal component located between the femoral and tibial components for transmitting a load therebetween, said meniscal component having depressions for receiving the condylar surfaces, and being arranged for sliding movement in a generally anterior-posterior direction on said tibial platform; and (d) guide means associated with said platform and engaging in a recess in the meniscal component between said depressions, wherein said meniscal component is guided for sliding movement in an anterior-posterior (a-p) direction but with restricted rotational motion.

Normally, the condylar surfaces of the femoral component are shaped to conform quite closely with the depressions or concavities in the meniscal component over a large amount of flexion so as to minimise stress high points. Such high conformity is compensated by the sliding freedom of the meniscal component on the tibial platform.

Preferably, the tibial bearing surface, when viewed in one or more sagittal sections, has a radius of curvature which substantially corresponds with the radius of the bearing surface of the femoral component. However, there may be differences in the profiles of the sagittal sections, provided that contact is substantially continuous from posterior to anterior. Indeed, this is desirable to provide for the required laxity in the joint. For example, the radii of the femoral sagittal sections may be slightly smaller than the radii of the corresponding sections of the tibial bearing surface, so as to allow sufficient clearance for taking up differences in surgical placement of the two components of the prosthesis, and allowing adequate laxity for normal functions.

Where the cruciate ligaments are retained in the fitting of the prosthesis, the femoral component portion which encases the resected condyles may be formed with a slot to permit passage of the ligaments. However, many surgeons prefer to resect the cruciate ligaments and in this case, the femoral component may be continued in the distal/posterior region across the full width, i.e. in the lateral-medial direction.

The extent to which the constant radius of the femoral component in sagittal planes extends around the distalmost point is the amount sufficient to give the desired degree of flexion of the joint.

Preferably, the anterior face of the femoral component is formed with a patella groove which is shaped so that there is contact between the patella and the groove through all degrees of flexion.

Conformity of the femoral and tibial bearing surfaces during all stages of flexion gives increased contact area between the metal and plastic meniscal bearing surfaces, leading to reduced wear and deformation. Also, as the sagittal curvature of the tibial component is upwardly concave, the up-sweep of the tibial bearing surface posteriorly and anteriorly gives increased stability in anterior-posterior, medial-lateral and internal-external rotations. Close contact between the patella (whether natural or artificial) with the patella groove during all stages of flexion also contributes to greater stability of the joint.

The tibial component of the knee prosthesis comprises a metal platform which is adapted to be secured to a resected tibia and a plastics meniscal bearing component is mounted for sliding movement thereon, and is guided in a substantially a-p direction. The mating surface between the plastics component and the metal platform may be flat or, alternatively, may be substantially cylindrical, with the axis of the cylinder extending in a lateral-medial line and the radius of the cylinder being larger than the maximum sagittal radius of the bearing surface between the femoral and tibial components. The curvature of the bearing surface between the femoral component and the tibial component in the sagittal plane is in the same sense as the curvature of the cylindrical mating surface, between the plastics component and the metal platform.

By providing for sliding movement in the anterior-posterior direction, the prosthesis has freedom of movement in the anterior-posterior direction, which allows a higher degree of flexion, while reducing shear stresses in the component-bone interfaces.

The provision of a cylindrical bearing surface between the plastics component and the metal platform viewed in a sagittal plane has the advantage that it constrains the movement in the anterior-posterior direction. Also, the upwardly curved interface between the plastics component and the metal platform introduces increasing constraint due to gravity forces as the plastics bearing component displaces further away from its central position.

However, a concave platform is not essential and flat tibial platforms have the advantage that it is easier to provide for a degree of relative rotational motion between the meniscal component and the tibial platform.

It has been found to be advantageous to provide for a degree of rotational movement of the meniscal component on the tibial platform of up to about ±15°, more often about ±10°, in addition to a degree of a-p sliding motion. Generally, the degree of external rotation should be greater than the internal. It has been found to be advantageous to bias such rotational motion so that the meniscal component and femoral component rotates about a vertical axis displaced medially of an a-p axis extending generally through the center line of the tibial platform. This tends to increase the stability of the joint because the medial condyle and the corresponding tibial articular surface are broader and the rotation of the natural knee is about a medially displaced axis.

In accordance with a feature of the invention, this rotational bias is very simply achieved by providing stop means to constrain movement of the meniscal component on the medial side of the prosthesis. Conveniently, an abutment is positioned to project upwardly from the tibial platform on the posterior side and medially of the center line.

Various features and advantages of the present invention will become clearer from the following description and accompanying drawings in which:

FIG. 1(a) is a perspective view of a normal knee which is flexed at 0°.

FIG. 1(b) is a perspective view of a normal knee which is flexed at 30°.

FIG. 1(c) is a perspective view of a normal knee which is flexed at 60°.

FIG. 1(d) is a perspective view of a normal knee which is flexed at 90°.

FIG. 1(e) is a perspective view of a normal knee which is flexed at 120°.

Figure 2B:
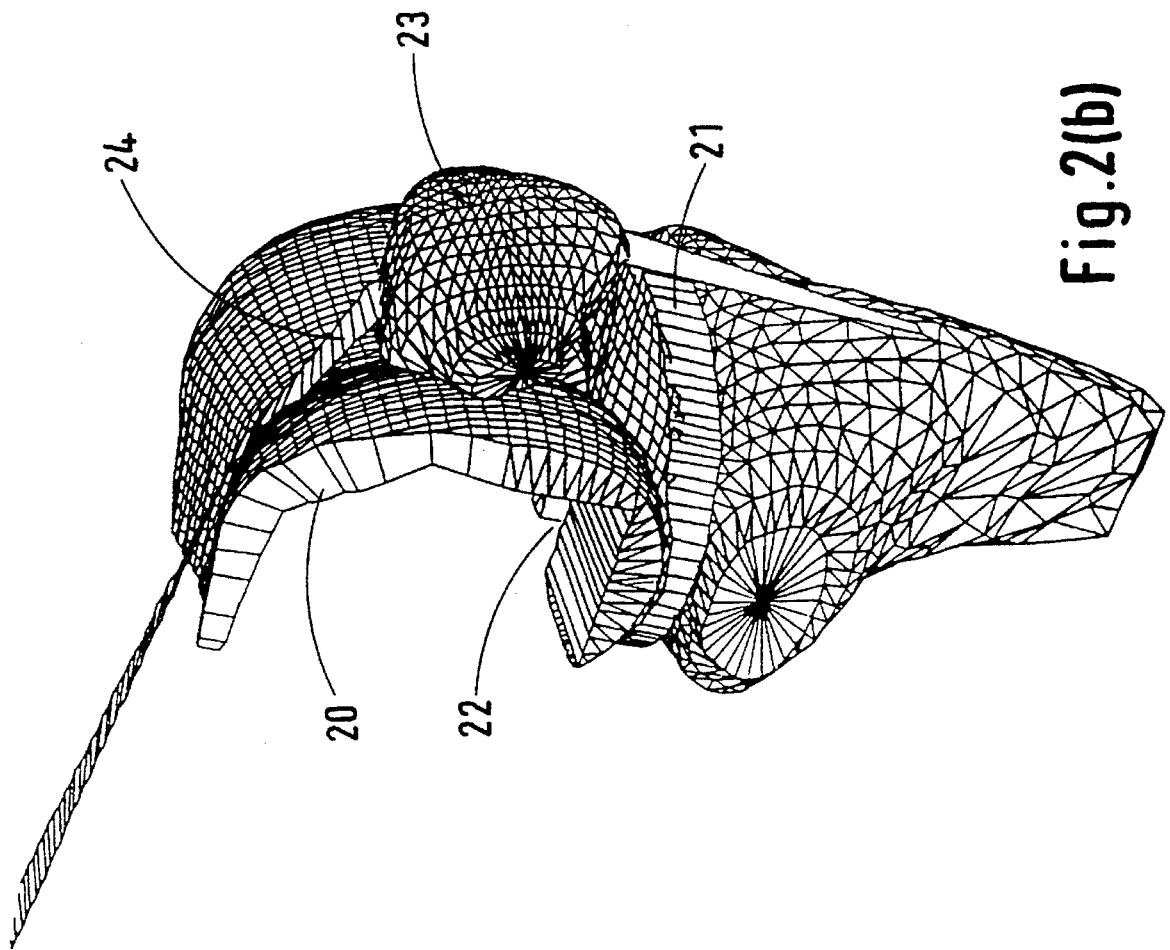
Figure 2A:
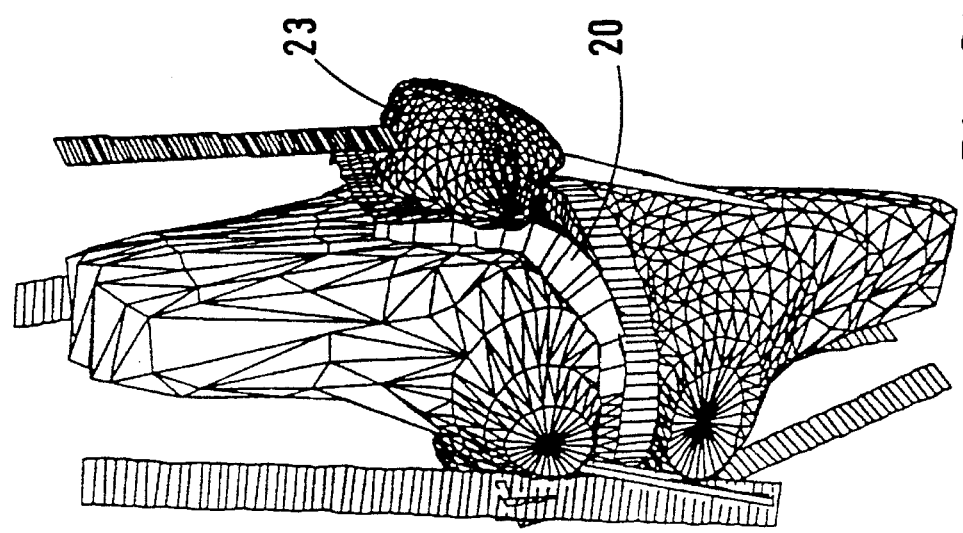
Figure 3A:
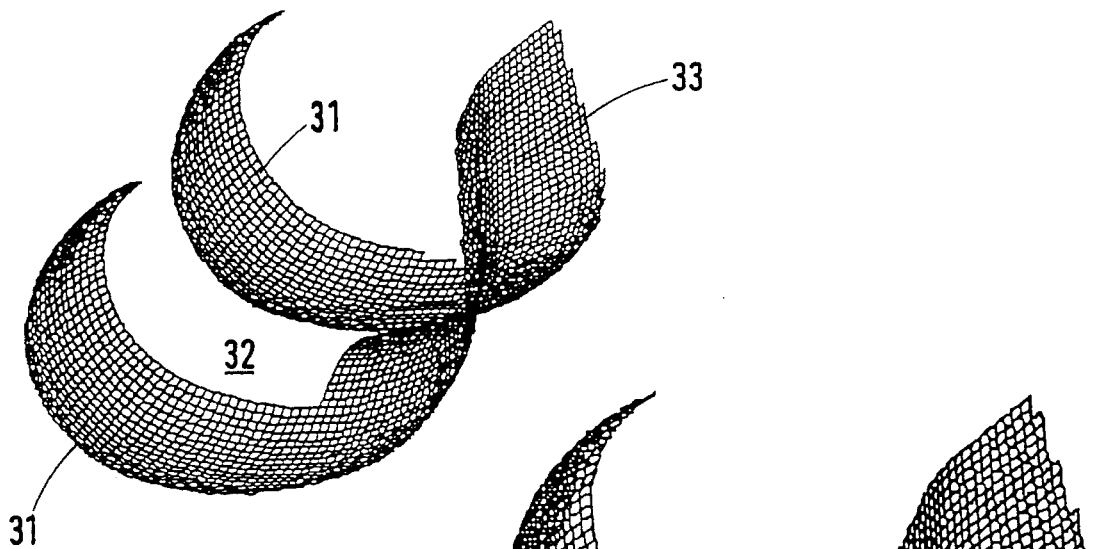
Figure 3B:
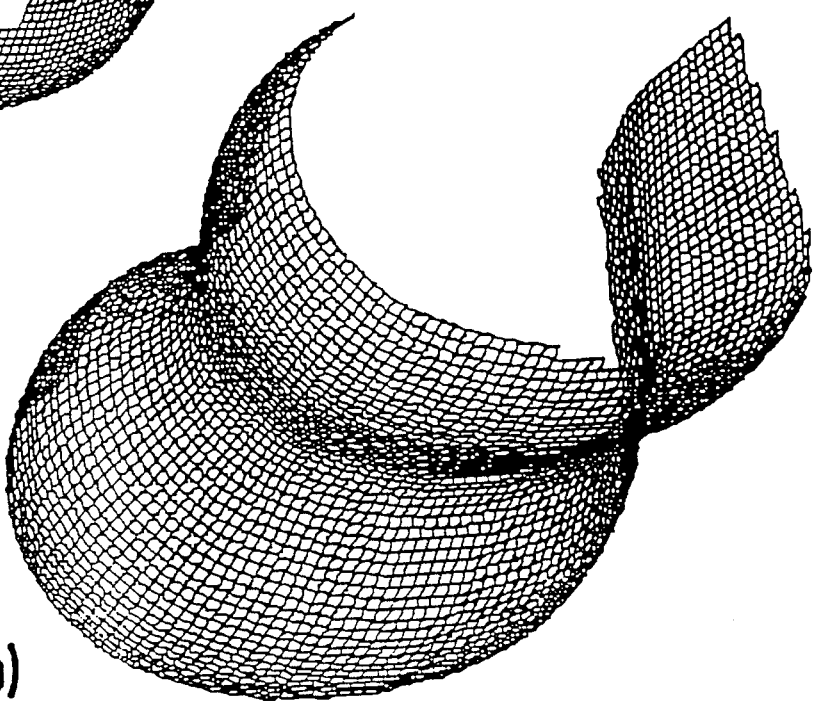
Figure 3C:
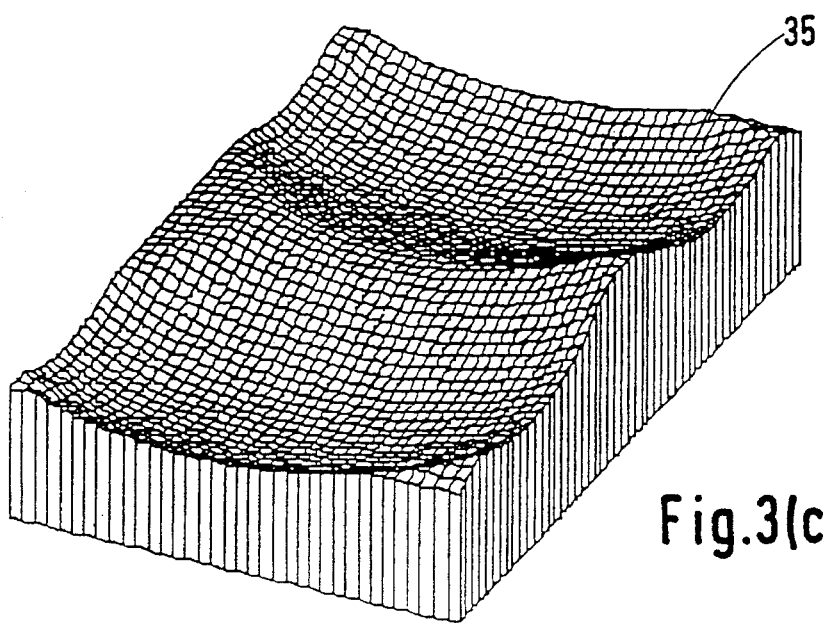
Figure 4A:
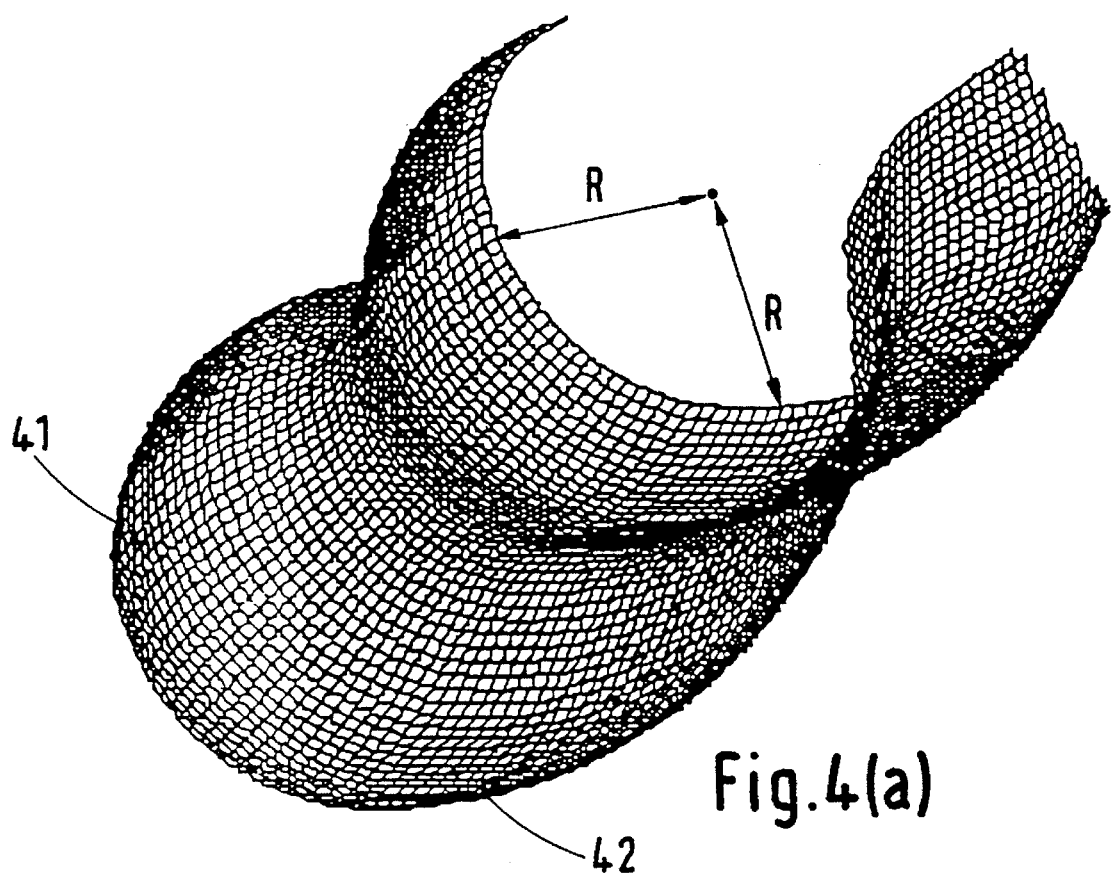
Figure 4B:
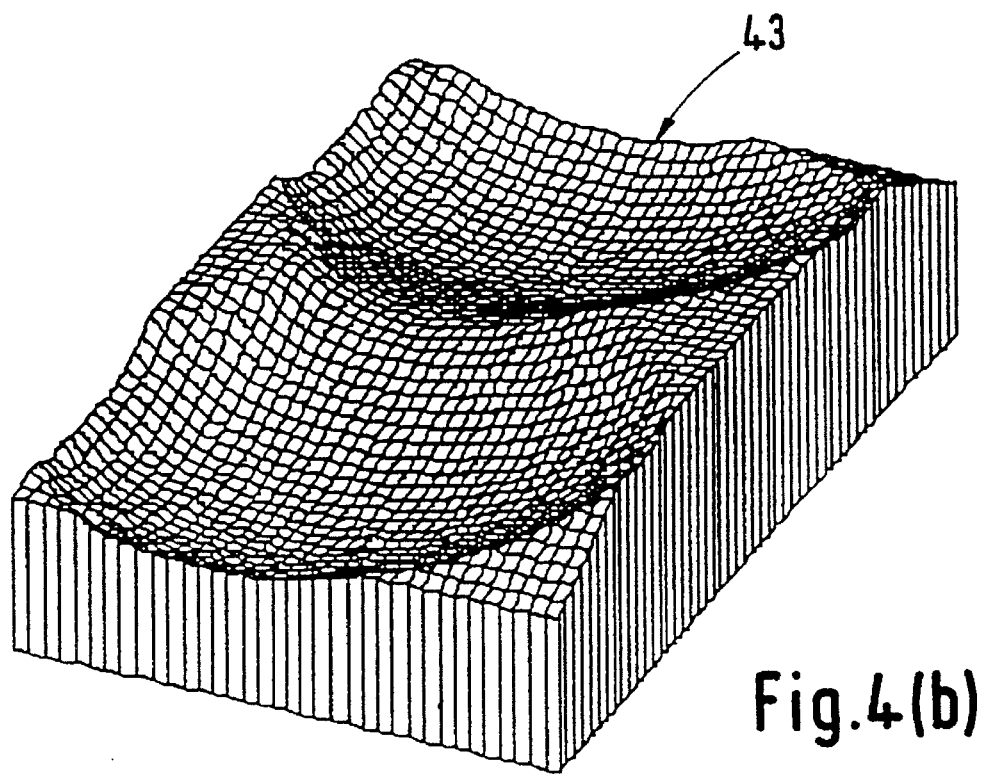
Figure 5D:
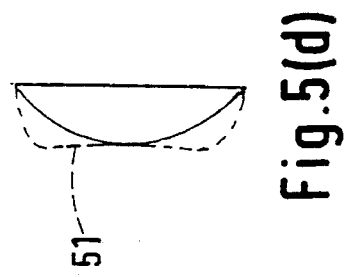
Figure 5C:
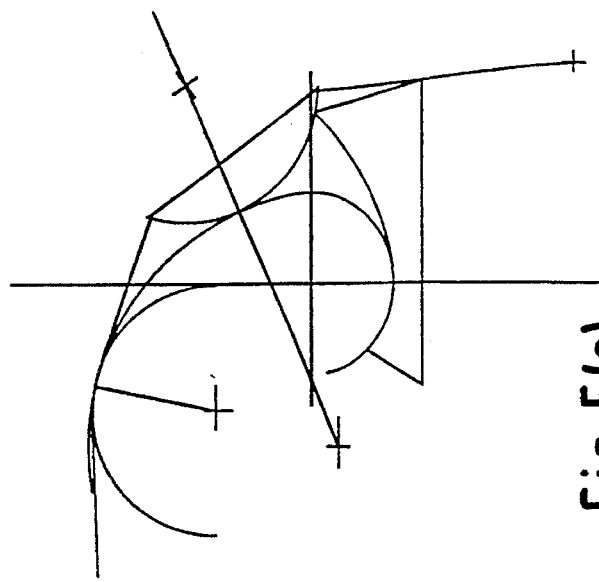
Figure 5B:
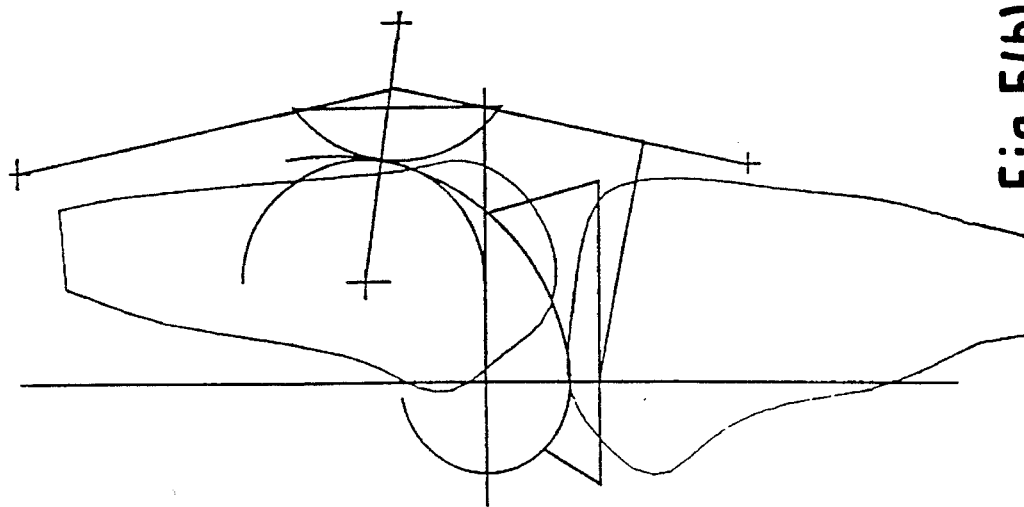
Figure 5A:
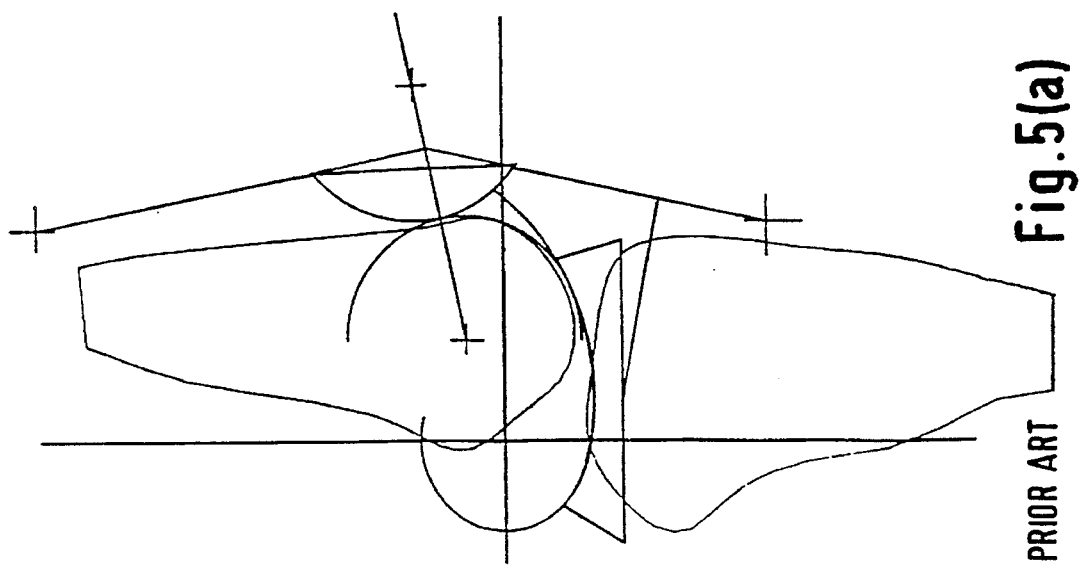
Figure 6:
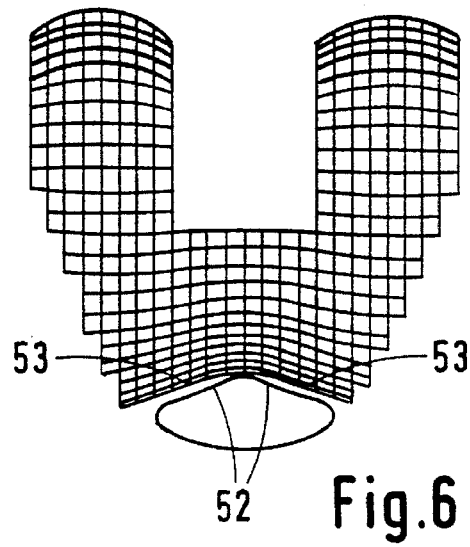
Figure 7A:
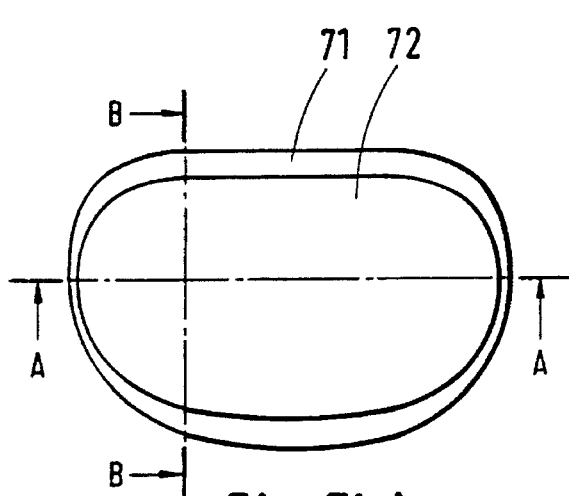
Figure 7B:
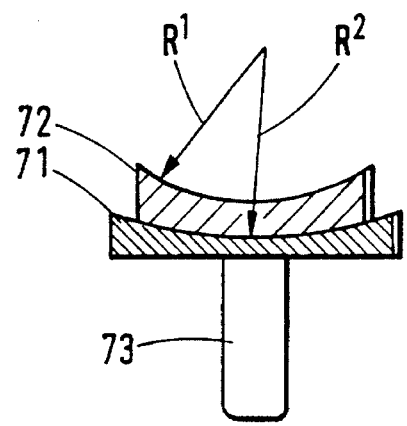
Figure 7C:
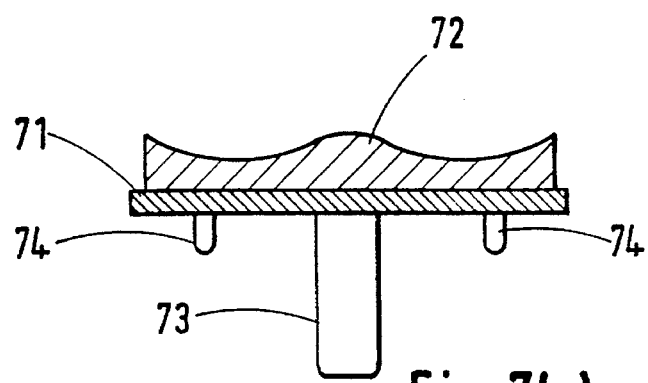

FIG. 2(a) is a perspective view of a knee fitted with a prosthesis in accordance with the invention at zero flexion, FIG. 2(b) is a perspective view of the knee (with the femur removed for clarity), fitted with same prosthesis at approximately 90° flexion, FIG. 3(a) is a perspective view of a femoral component in accordance with a first embodiment of the invention, FIG. 3(b) is a view similar to FIG. 3(a) of a modified form of the femoral component, FIG. 3(c) is a perspective view of a tibial component intended for use with the femoral component of FIG. 3(b), FIG. 4(a) is a perspective view similar to FIG. 3(a) of a further embodiment in accordance with the invention and FIG. 4(b) shows a perspective view of a corresponding tibial component, FIG. 5(a) shows, diagrammatically, a sagittal view of a conventional design, FIG. 5(b) shows, diagrammatically, a first sagittal view of a prosthesis in accordance with the invention, FIG. 5(c) shows, diagrammatically, a second sagittal view of a prosthesis in accordance with the invention, FIG. 5(d) is a sagittal view of the profile of a patella replacement (in broken lines) compared with a conventional replacement (full lines), FIG. 6 is an underside view of a femoral component showing the conformity of the patella with the patella groove, FIG. 7(a) is a plan view of a tibial component in accordance with the invention, FIG. 7(b) is a section taken on the line B—B in FIG. 7(a) with the invention, FIG. 7(b) is a section taken on the line B—B in FIG. 7(a), FIG. 7(c) is a section taken on the line A—A in FIG. 7(a), FIG. 8(a) is a plan view of a modified tibial component, FIG. 8(b) is a section taken on the line A—A in FIG. 8(a) but with the anchoring pegs omitted, FIG. 9(a) is a plan view of a further embodiment of a tibial component, FIG. 9(b) is a view taken on the line A—A in FIG. 9(a), and FIG. 10 is a view similar to FIGS. 7(b), 8(b) and 9b) of a modified tibial component showing alternative ways of guiding the plastics component.

Figure 11A:
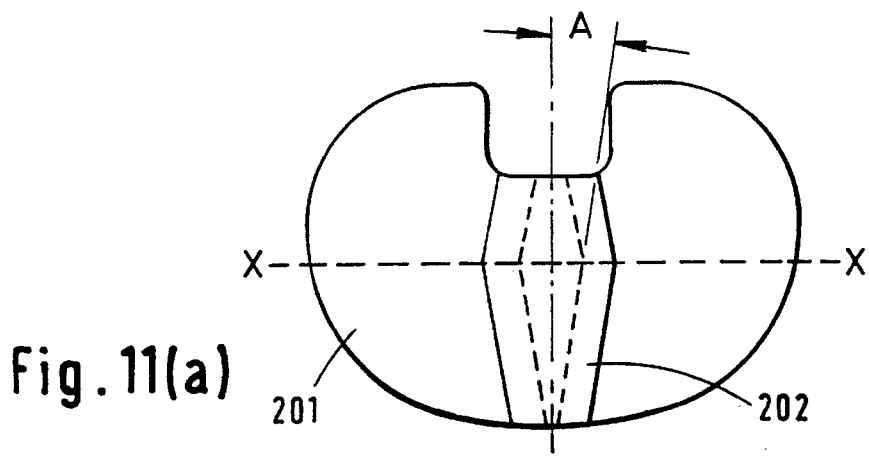
Figure 11B:
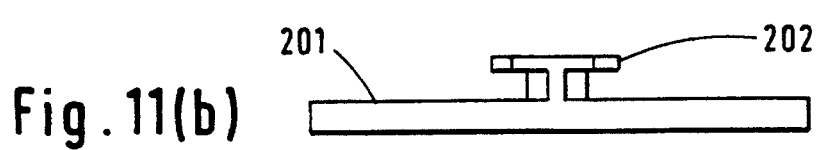
Figure 11C:
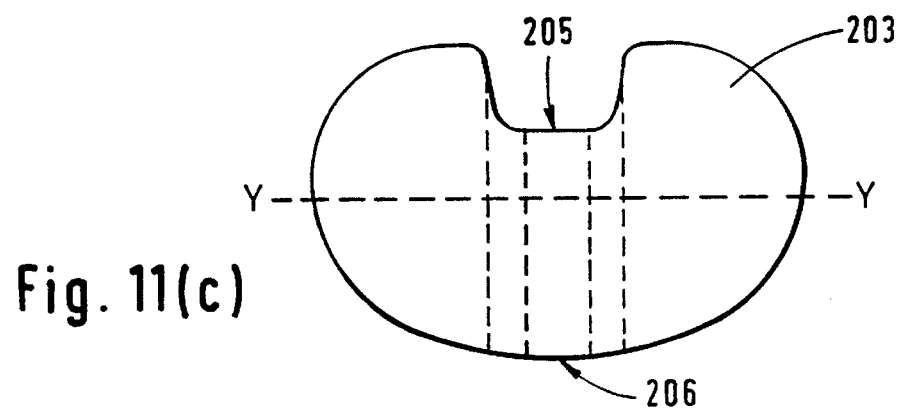
Figure 11D:
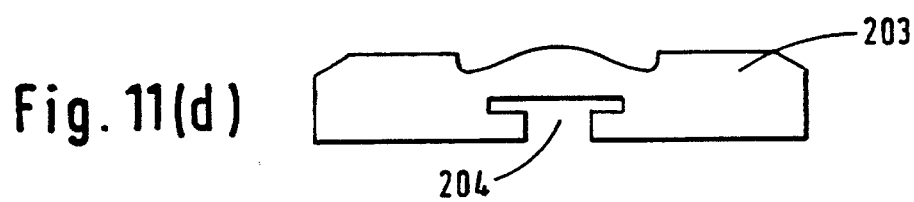
Figure 11E:
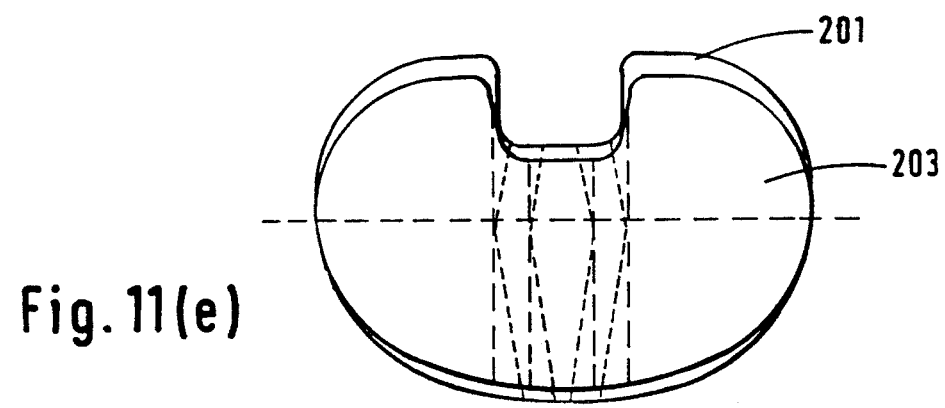
Figure 12A:
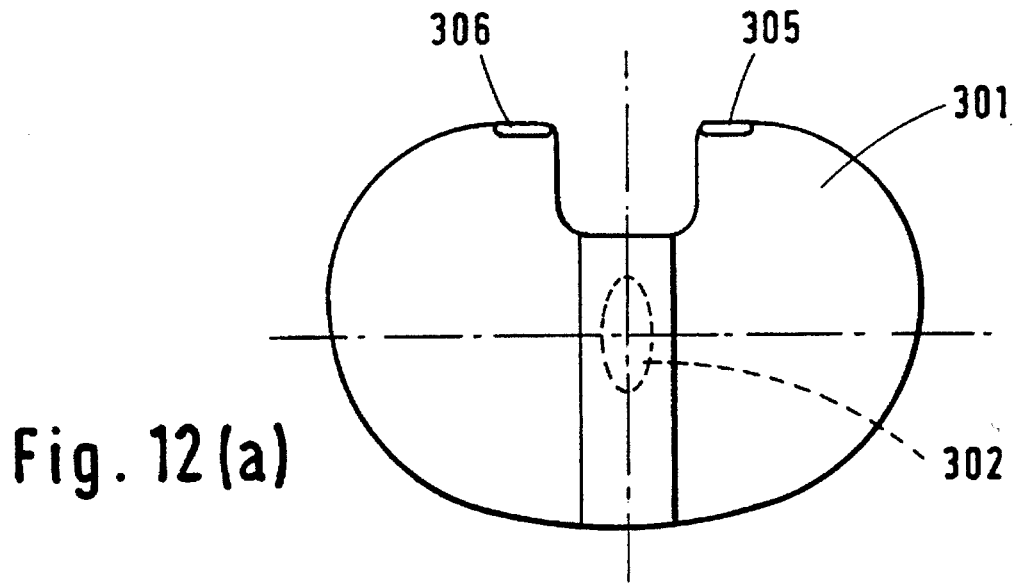
Figure 12B:
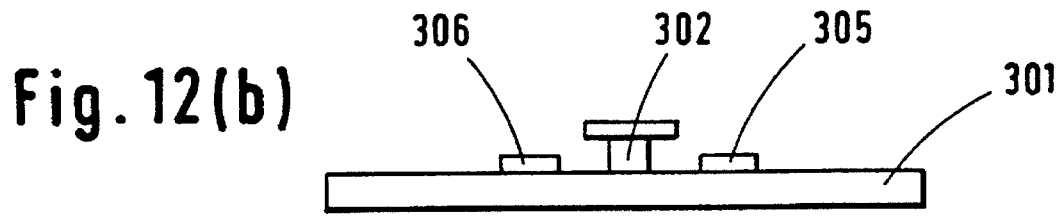
Figure 12C:
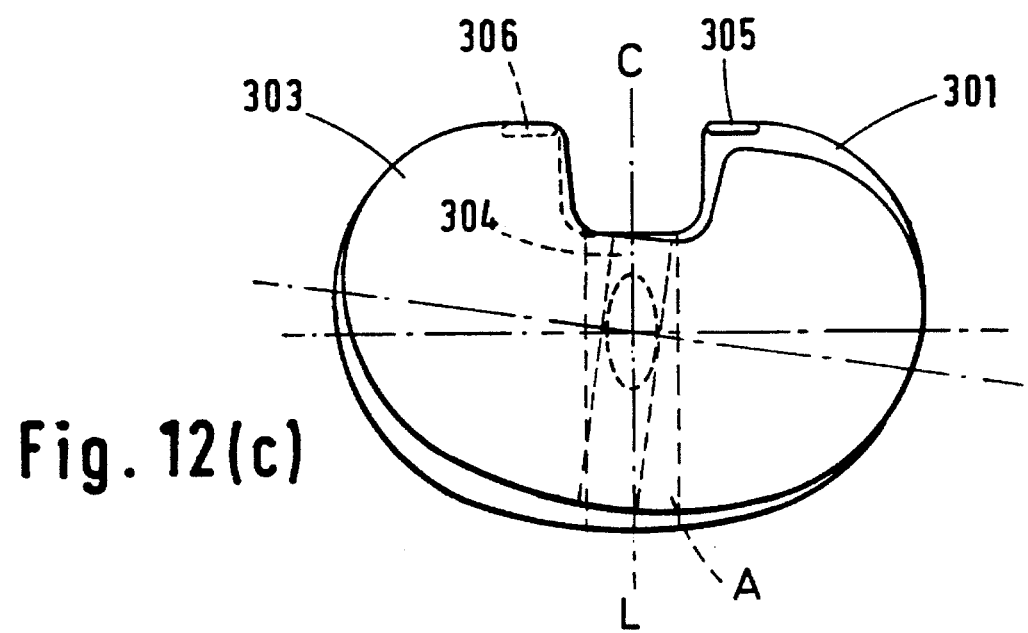
Figure 13A:
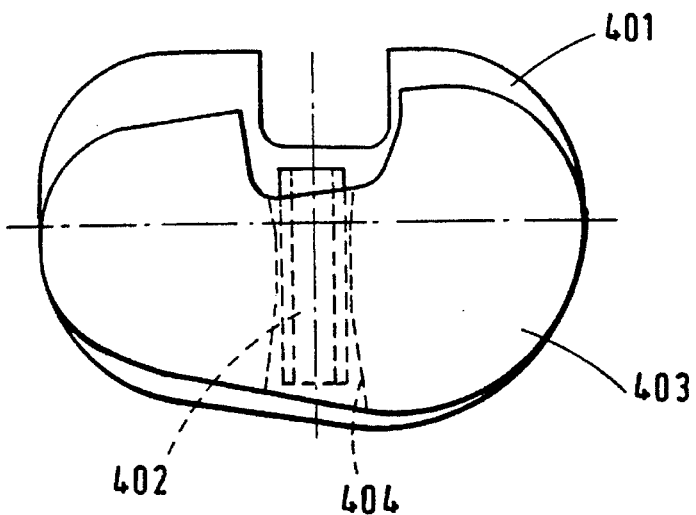
Figure 13B:
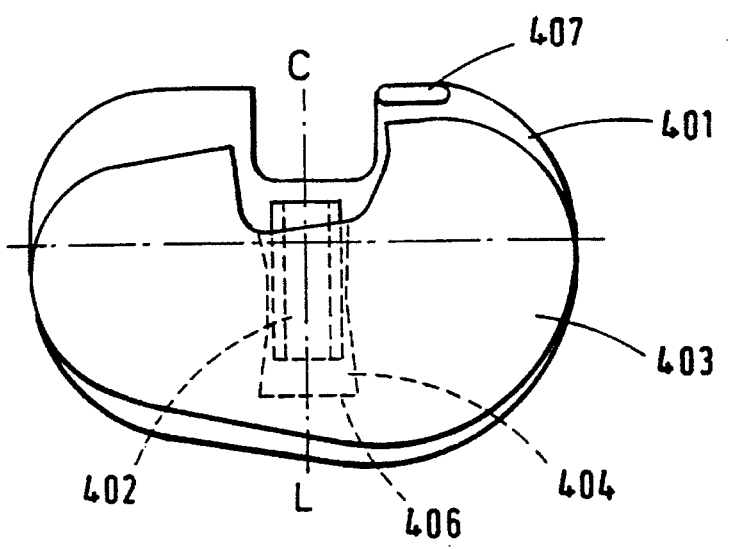
Figure 14:
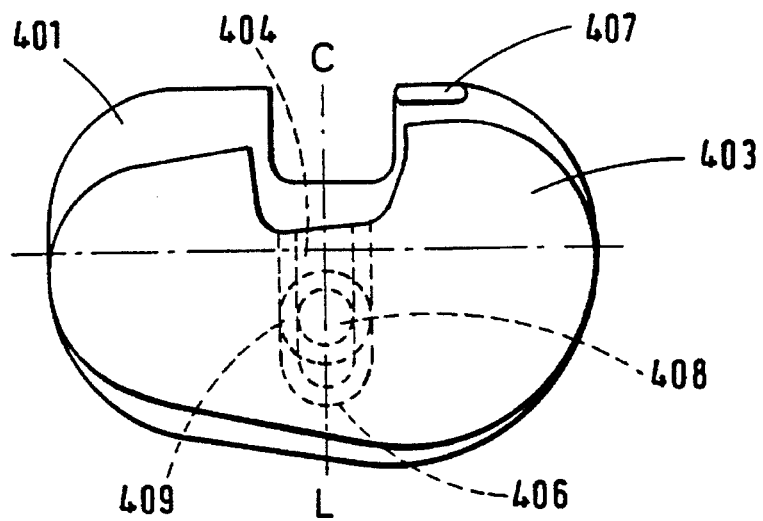
Figure 15:
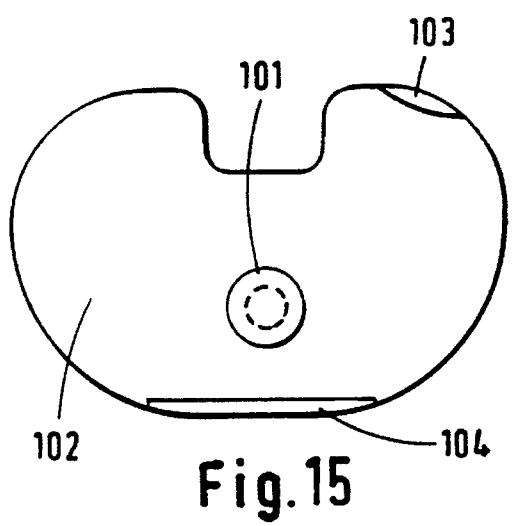
Figure 15B:
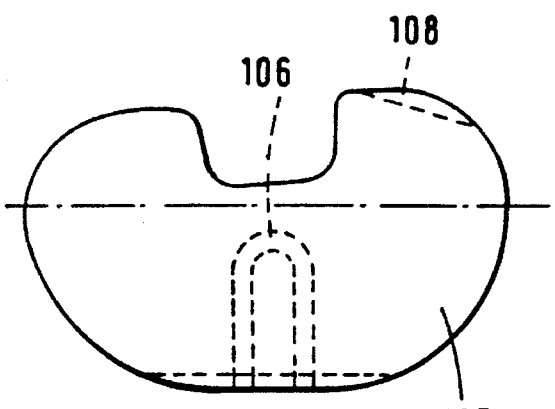
Figure 15A:
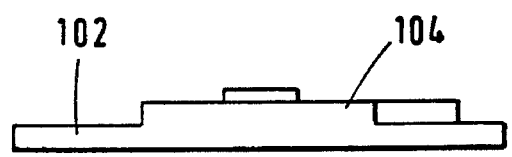
Figure 15C:
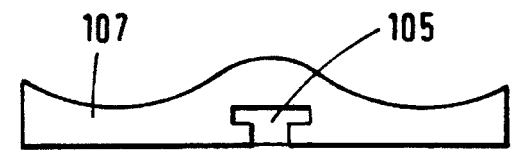
Figure 15D:
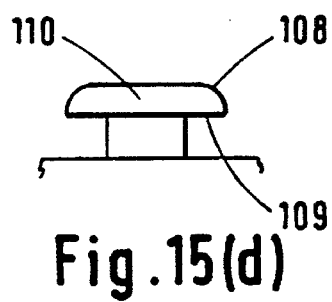
Figure 15F:
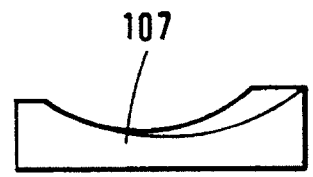
Figure 15E:
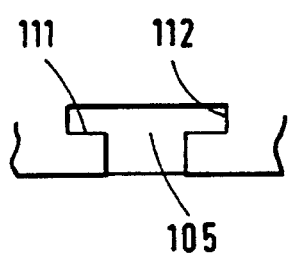

FIG. 11(a) is a plan view of another embodiment of the tibial component,

FIG. 11(b) is a section taken on the line X—X in FIG. 11 of the tibial base plate, FIG. 11(c) is a plan view of the plastics meniscal component intended to be supported on the tibial base plate of FIG. 11(a), FIG. 11(d) is a section taken on the line Y—Y in FIG. 11(c), FIG. 11(e) is a plan view showing the plastics meniscal component mounted on the metal base plate, FIG. 12(a) is a plan view of a further embodiment of the tibial base plate, FIG. 12(b) is a view of the base plate of FIG. 12(a) seen from the anterior side, FIG. 12(c) is a plan view of a meniscal component mounted on the base plate of FIG. 12(a), FIG. 13(a) is a plan view of a still further embodiment of a tibial component showing a plastics meniscal component supported by a tibial platform, FIG. 13(b) is a similar view of a modified form of the embodiment of FIG. 13(a) in which the tibial plate incorporates a posterior medial stop, FIG. 14 is a further modification in which the guide rail is replaced by a guide stud, FIG. 15 is a plan view of a further embodiment of a tibial platform, FIG. 15a is an elevation in the direction of the arrow X in FIG. 15, FIG. 15b is a plan view of the meniscal component, FIG. 15c is a sectional view on the line B—B in FIG. 15b, FIG. 15d is an elevation of the T-shaped stud on an enlarged scale, FIG. 15e is a sectional view of the slot in the meniscal component on a similar scale to FIG. 15d, and FIG. 15f is a pair of sectional views taken on the lines L & M in FIG. 15c.

FIG. 1(a) of the accompanying drawing shows a sagittal view of a natural knee which is flexed at 0°. FIG. 1(b) shows a sagittal view of the natural knee which is flexed at 30°. FIG. 1(c) shows a sagittal view of the natural knee which is flexed at 60°. FIG. 1(d) shows a sagittal view of the natural knee which is flexed at 90°. FIG. 1(e) shows a sagittal view of the natural knee which is flexed at 120°. The distal end 1 of the femur 2 can be seen to have a larger radius than the posterior 3. At zero degrees flexion, the larger radius distal end 1 contacts the top of the tibia 4, resulting in greater conformity and a greater area of contact. Other structures increase the contact area, notably the menisci, which are deformable discs interposed between the femoral and tibial condyles. When the knee is flexed, the femoral-tibial conformity is reduced, which would reduce the contact area and result in high contact stresses. However, the deformable menisci take up the shape between the femoral and tibial surface and once again spread the load. If the menisci are removed for injury, in later years, there is an increased chance of osteoarthritis.

The knee displays both laxity (which can be termed freedom of motion) and stability, which is the control of displacements and rotations to within acceptable limits. Laxity can include linear or rotational translation in any of the three mutually perpendicular coordinate axes. For purposes of the invention, laxity is only considered in anterior-posterior displacement, medial-lateral displacement and internal-external rotation, these being the most significant. The anterior-posterior stability is provided mainly by the cruciate ligaments. The anterior cruciate 5 can be seen in FIG. 1, especially at the higher flexion angles. Rotational stability is provided by a combination of the cruciate and collateral ligaments. The muscles also play an important role in providing stability. The joint surfaces contribute to stability as force is applied across the joint, due to the slight dishing of the surfaces and the deformability of the articular cartilage. The laxity is due to the elastic extensibility of the ligaments, the joint surfaces, and other soft tissues surrounding the joint.

The patella is an important bone which transmits the force between the quadriceps and the upper tibia. In broad terms it can be regarded as a pulley, sliding up and down on the front of the femur. The patella fits closely into a groove on the front of the femur, such that the contact areas are broad bands across the width of the patella. Beyond about 90 degrees of flexion, the contact splits into two parts as the patella straddles the intercondylar groove.

When a condylar replacement is introduced (FIG. 2), a femoral component 20 is attached to the end of the femur and a tibial component 21 to the upper part of the tibia. Normally, the ends of the femoral condyles are resected and shaped to receive the femoral component and held in place with bone cement and/or pegs extending into the condyles. The collateral and cruciate ligaments can be preserved by providing a slot 22 in the femoral component, although in most designs, either the anterior is resected, or both cruciates are resected. The patella 23, either the natural patella or a replacement, fits into the groove 24. When the knee is flexed with conventional prostheses, there is now a distinct lack of conformity between the femoral and tibial surfaces, with the result that the contact stresses on the plastic surface are high, leading to failure due to breakdown of the plastic in many cases.

Prior designs suffer from a number of problems; for example there is no meniscus to spread the force as in the normal knee. If the anterior cruciate is resected, there should ideally be a posterior upsweep of the tibial plastic surface to compensate, and if the posterior cruciate is resected also, an anterior upsweep is needed. In angles of flexion beyond about 90 degrees, there are two separate contacts on the patella component, leading to high stresses and deformation, and also sometimes 'catching'.

A typical femoral component in accordance with the invention is shown in FIG. 3(a). The condylar surfaces 31 resemble the anatomical, especially in the sagittal view, and there is a cut-out or slot 32 for one or both cruciate ligaments. A patella groove 33 is continuous down to the cut-out 32 after which it splits. The larger femoral component in FIG. 3(b) now has continuous surfaces throughout, including the patella groove, but is otherwise the same. Such a configuration requires resection of both cruciate ligaments. The femoral shape is then used to computer-generate a tibial surface 35, based on input laxity requirements in anterior-posterior displacement and internal-external rotation. A computerized method of generating tibial surfaces is described in U.S. Pat. No. 4,822,365. The new femoral shape has two advantages. First, the contact on the tibial surface can now be spread over the entire width of the tibial surface, thus increasing the contact area. Second, the patella has a continuous track, and can maintain a broad contact area throughout motion, without a split of the contacts at higher flexion. However, there is still the disadvantage that the radius of curvature of the distal femur is greater than the posterior, such that once flexion is initiated, the smaller femoral radius contacts the tibia giving a reduction in contact area.

FIGS. 4(a) and 4(b) shows one solution to this problem. Here, the radius of the posterior portion 41 of the femoral component has been carried round to the distal femur 42. Now there is a constant radius R for contacting the tibial surface 43. A surface computer-generated with this component is clearly more dished than the previous component and provides an increase in the contact area throughout. The reduction in the contact stresses are calculated to be significant. Another benefit of the new surfaces is the enhanced stability. In the surfaces of FIG. 3, it can be imagined that the flexed femur can slide forwards on the tibia with relatively little resistance. However, in FIG. 4, the anterior sliding is much more restricted because of the steeper slope of the anterior tibial surface.

Certain characteristics of this design form are illustrated in FIG. 5 which shows sagittal views of a standard design (FIG. 5(a)) and a design in accordance with the invention, (FIGS. 5(b) and 5(c)). The differences in the distal femoral radii can be clearly seen. This change in distal radius has three consequences. More resection of anterior bone is needed for installation, although this is not a serious problem. The second problem is that the patella mechanics are altered. An important parameter of patella function is the lever arm, because this helps to determine quadriceps efficiency. With the knee at zero flexion, the lever arms are similar, but in mid-flexion (around 45 degrees), it can be appreciated that the lever arm of the design on the right will be reduced. This is not a significant problem, since a convenient remedy is to treat the bearing surfaces and patella surfaces as separate. The patella surface would then protrude as normal, in between the bearing surfaces. Such a solution reduces the width of the main bearing areas and may not represent an overall advantage. A final characteristic is that the femoral-tibial contact point is more posterior than normal. This has the advantage of improved quadriceps efficiency, as noted, but may result in upwards tilting of the front of the tibial component. If necessary, the position of the bottom of the curvature on the tibial surface could be moved anteriorly by 2–3 m which would alleviate this problem.

An improvement to the patello-femoral contact is apparent from FIG. 5. The normal dome-shape (FIG. 5(a)) has high conformity when seen in the overhead view (FIG. 6), but low conformity in the sagittal view. Several experimental and theoretical studies has shown that the angle through which the patella rotates relative to the femoral component in the sagittal plane is within 10 degrees (FIG. 5(b) and 5(c)). This means that a high degree of conformity can be designed into the patella with no loss in freedom of motion. The new sagittal profile of the patella is shown dotted in FIG. 5(d). As can be seen, instead of having a continuous convex shape in sagittal view, it has a flattened inner face 51 and outwardly extending surfaces 52 (FIG. 6), giving greater conformity with the sides of the patella groove 53. Such increase in conformity leads to greatly reduced contact stresses. A consequence of such a design is that if surgical placement is rotationally incorrect, there would be restriction of motion. However, the curvatures can be adjusted to allow for an appropriate margin of error.

The above design form in accordance with the invention is most suitable when the anterior and posterior cruciate ligaments are resected. In this case, there will still be sufficient anterior-posterior laxity (approximately 5 mm total) and rotational laxity (+−12 degrees), without restriction from taut ligaments. Such laxity will also be sufficient for activities of everyday living. The disadvantage is that the components are relied upon for stability, and in the long run, this may lead to problems with the fixation of the components to the bone. In addition, resection of the cruciates is believed to reduce the proprioceptive response of the knee with consequent compensatory gait patterns. A further disadvantage is that extremes of motion which occur during more demanding activities may be restricted, a possible disadvantage to younger or active patients. One approach to this problem is to use a meniscal bearing type of arrangement, already embodied in several designs, notably the LCS New Jersey, the Oxford, the Minns, and the Polyzoides—see U.S. Pat. Nos. 4,340,978 and 4,085,466. In these designs, anterior-posterior translation and internal-external rotation is completely unrestricted, except by impingement of the plastic bearing pieces onto capsular soft tissue at the anterior and posterior of the tracks. An important restriction to the designs however is that both the anterior and posterior cruciate ligaments are required, otherwise the stability is insufficient and the plastic bearings can dislocate.

At least two of the designers of the above-named devices have considered the distal-posterior radius problem of the femoral component. If the radii were different, as in FIG. 3, then the main advantage of the meniscal bearing concept, complete contact and low stresses, would be lost. U.S. Pat. No. 4,340,978 shows the meniscal bearing concept. In FIGS. 1 and 3 of this U.S. Patent, the Oxford scheme is shown in U.S. Pat. No. 4,085,466. A uni-condylar femoral component has a spherical radius, but does not carry up into a patella flange. The New Jersey design opts for smaller radii posteriorly than distally (FIG. 22), and illustrates the loss of full conformity in flexion in FIG. 33.

One further improvement provided by the present invention is to provide for sufficient anterior-posterior and rotational stability so that the prosthesis can be used with or without the cruciate ligaments, and to provide complete femoral-tibial conformity throughout the entire range of flexion. In essence, it consists of making the polished metal platform for supporting the plastic bearing piece or pieces concave when seen in the sagittal view. The effect will be to offer steadily increasing resistance to displacement away from the neutral position. In this respect, the stability and laxity characteristics can be made similar to that of a normal knee, or to a usual type of condylar prosthesis. The schematic views (FIG. 7(a)) shows the overall arrangement seen in plan view, with a metal plate or platform 71, for attachment to the tibia, having a polished cylindrical surface on the top of the plate and a plastic bearing component 72 which slides on the polished surface. The femoral condylar surfaces are intended to have a constant sagittal radius in the region which articulates against the plastic surface, and conform closely with the tibial surface in both frontal and sagittal planes. An important feature is that the radius of the plastic surface is smaller than that of the cylindrical surface. The cylindrical shape of the bearing surfaces is shown in FIG. 7(b) in which $R^2$ is greater than $R^1$. FIG. 7(c) shows the medial-lateral section and a central fixation peg 73 and anti-rotation pegs 74 to prevent the platform 71 rotating on the tibia.

For a one-piece plastic component of the kind shown in FIGS. 7(a)–7(c), rotation is not possible without loss of complete contact on the cylindrical surfaces. However, anterior-posterior displacement is possible. The arrangement providing anterior-posterior motion from a one-piece plastics tibial bearing component is shown in FIGS. 8(a) and 8(b). The metal platform 81 supports a plastics bearing component 82 which is guided for anterior-posterior motion on a rail 83 fixed or integral with the platform 81. The platform may be curved in the sagittal plane as shown in FIG. 7(b) or be planar. It may be convenient to constrain anterior-posterior motion within limits by providing suitable stops, e.g by means of an upstanding post 84 secured to the platform and an elongated hole 85 in the bearing pad 82. Thus, the pad 82 may move freely in an anterior-posterior direction into the post 84 abutting one of the ends of the elongated hole. An alternative method of providing stops is indicated in dotted lines in FIG. 8(a) in which the recess in the plastics meniscus component 82 has a wall 86 against which the end face of the rail 83 abuts to limit the anterior-posterior movement in one direction.

Separate plastics pads 91,92 (see FIGS. 9(a) and 9(b)) are an alternative arrangement supported on a common metal platform 93. Linear guidance is achieved by a metal rail 94, leaving a small clearance between the pads and the rail. Again, the bearing surface between the platform and the pads may be curved or planar. For two separate plastic components, both anterior-posterior translation and internal-external rotation are possible. For the latter, for bearing surfaces spaced apart 48 mm, only 0.8 mm inwards motion per side is needed to accommodate up to about +−15 degrees of rotation.

Different ways can be envisaged to engage the plastic component and tibial platform.

Alternatively, the tibial platform may be flat and this has certain advantages including an easier construction for providing a-p sliding movement in conjunction with rotational movement. When flat tibial platforms are employed, a highly conforming femoral condylar bearing surface and corresponding meniscal component preferably completes the prosthesis. While it is possible to provide for guide means to project from the meniscal component and engage in a corresponding recess in the tibial platform, it is preferred to design the guide so as to be upstanding from the platform, e.g. on a rail or post and to engage in a slot or recess in the meniscal component. Conveniently, the guide means is located in the region of the center line of the platform and aligned for a-p sliding movement.

Different ways can be envisaged to engage the plastic components, such as by T-shaped metal rails, under which a plastic lip is captured. This is illustrated in FIG. 10, which is a view similar to FIG. 7(c). A tibial bearing pad 101 is supported for sliding anterior-posterior motion on platform 103 The pad 101 is trapped and guided by rail 102 having a 'T'-shaped profile section FIG. 10 also shows an alternative or additional trapping and guidance means by one or more lateral guides 104 having inwardly turned projections 105 which engage in slots in the plastics pad. A central guide rail is preferred since this is less prone to jamming.

Referring to FIGS. 11(a) and 11(b), these FIGS. show a top and front view respectively of the metal base plate 201 of the tibial component and indicates a rail member 202 which provides for guiding the meniscal component 203 thereon. As can be seen in FIG. 11(a), the rail member is tapered anteriorly and posteriorly so as to allow the meniscal component to rotate within limits on the tibial plate, as indicated by the angle A.

FIGS. 11(c) and 11(d) show respectively top and front views of the plastics meniscal component, and it will be seen that the meniscal component includes a parallel groove 204 which is 'T'-shaped in section and extends anteriorly and posteriorly of the meniscal component. The groove or slot is open at both ends (i.e. posteriorly 205 and anteriorly 206) but may, in some embodiments, be closed anteriorly. The rail slides within the 'T'-shaped groove or slot in the meniscal component and the arms of the 'T' prevent the meniscal component lifting off from the base plate and dislocating from the prosthesis.

FIG. 11(e) is a superimposed view of the meniscal component on the metal base plate and it will be seen that the meniscal component is smaller in overall area than the metal base plate in the a-p direction. This allows movement in the a-p direction without losing support from the metal base plate. In general, the tibial component is designed so that the bias is for more posterior sliding movement to allow for the desired roll back of the joint in normal flexion.

The parallel 'T'-shaped groove or slot in the meniscal component allows the plastic meniscal component to slide in an a-p direction on the metal base plate, and to rotate through an angle A as shown in FIG. 11(b). The width of the rail is such that it is always trapped in the upper slot of the plastics component, even at full rotation.

Referring to FIG. 12, this shows a variation of the arrangement shown in FIG. 11 and constitutes a further embodiment of the present invention.

FIGS. 12(a) and 12(b) are respectively top and front views of the metal base plate and it will be seen that the arrangement is generally similar to that shown in FIG. 11, except that the metal guide rail has an elliptically shaped cup portion 302 which fits in a corresponding slot in the meniscal component. The slot 304 in the meniscal component 303 is slightly wider than the minor diameter of the elliptically shaped guide rail, so that this allows for some rotation of the meniscal component on the base plate through an angle A in each direction. The metal base plate also includes stops 305 & 306 on the posterior lobes which prevent the meniscal component rotating more than a predetermined amount, as well as limiting the sliding movement posteriorly. In a preferred embodiment, the metal stop is provided only on the medial side so as to bias the rotation about an axis medially displaced from the center line C-L of the platform.

Further embodiments are shown in FIGS. 13(a) and 13(b) and 14 of the accompanying drawings. Referring to FIGS. 13(a) and 13(b), these show a meniscal plastics 403 component which is guided for movement on a rail 402 extending in the a-p direction and upstanding from a platform 401. As can be seen, instead of tapering the rail to allow rotational movement of the meniscal component on the platform in FIGS. 13(a) and 13(a), the rail is rectilinear and the slot 404 is relieved anteriorly and posteriorly to provide limited rotational freedom. The geometry of the slot in FIGS. 13(a) and 13(b) provides for an external rotation of about 10° and an internal rotation of about 5°.

The structure shown in FIG. 13(b) differs from that shown in FIG. 13(a) in that the slot 404 in the meniscal component 403 is blind at one end 406, which limits the posterior displacement of the component. Also, an upstanding abutment 407 is provided on the medial posterior side of the tibial plate, to limit medial roll back and to induce rotation about a medially displaced axis.

The arrangement shown in FIG. 14 is generally similar to that shown in FIG. 13(b), except that the rail is replaced by a peg 408 upstanding from the platform and fitted with a circular cap 409 for trapping the meniscal component on the platform. The platform then is guided for movement in the a-p direction by relative sliding movement of the peg in the slot 404 in the meniscal component. Posterior displacement is limited by the blind end 406 in the slot in the meniscal component and rotation of the component on the platform is limited by the single posterior medial abutment 407. In a modified embodiment, the slot 404 may be blind at the other end so that anterior displacement is limited by the blind end. It will be appreciated that restricting motion of the meniscal component posteriorly by provision of the blind end or stop 406 compensates for resection of the anterior cruciate ligament. Similarly, restricting motion anteriorly by provision of the stop 407 compensates for loss of the posterior cruciate ligament. Similar compensation is achieved by provision of suitable stops in the other embodiments illustrated herein.

Since in the embodiments of FIGS. 13(b) and 14 a stop is provided only on the medial side of the platform, the tibial components need to be handed for left and right legs. One possible way of overcoming this problem would be to provide holes in the medial and lateral sides of the tibial plates and fixing means so that the surgeon or his assistant could fit the abutment into the appropriate side of the plate before fitting the prosthesis.

Referring to FIGS. 15 and 15a, a generally asymmetrical tibial platform is shown in this embodiment, which may avoid the need for different manufacturing processes for the left and right knees. The dimensions given in these figures (which are in millimeters) indicate approximate sizes of the various parts. An upstanding 'mushroom' shaped stud 101 is located on the center line of the platform 102 (although it could be displaced slightly medially). A posterior abutment 103 is formed on the medial side of the platform in order to limit posterior sliding motion on the medial side. As can be seen, the abutment is rounded so that the meniscal component moves smoothly over its surface.

The anterior edge of the platform is formed with an upstanding rail 104. The purpose of this rail is to provide further security for the meniscal component by limiting rotation in extension. This may be particularly desirable where cruciate ligaments have been resected.

As in the embodiment of FIG. 14, the meniscal component is formed with a slot 105. However, in the embodiment of FIG. 15b etc., the slot is open in the anterior direction. The end of the slot 106 provides a stop for limiting anterior sliding movement of the meniscal component 107 on the tibial platform. As can be seen from FIG. 15b, the meniscal component is formed with a recess 108, having a flat surface for engaging the rounded surface of the stop 103 on the platform.

Because of the position stops 103 and 104, the stud 101 and the slot 105, it may be necessary to rotate the meniscal component in order to fit it to the stud. Alternatively, the slot may be designed so that the stud is a snap fit in the slot.

As can be seen in FIGS. 15d and 15e, the stud has a rounded top surface and corner 108, and a flat surface 109 to the cap portion 110. This gives more contact with the surface 111 of the groove 112. The dimensions of the stud and slot are such that there is a gap of about 0.1 to 0.3 mms between the stud and the slot giving a slight looseness and freedom of motion.

In the construction described above the femoral components and tibial metal platform are made from a metal acceptable for use for implantation in the human body and which are suitable for sliding contact with low wear. Examples are cobalt-chromium and stainless steels. The artificial patella (where present) and/or the plastics bearing components may be made from any biocompatible material capable of withstanding the imposed loads and providing appropriate bearing properties when in contact with a polished metal surface. Preferably, the plastics material should exhibit low friction properties under these conditions. Examples of suitable materials are ultra-high molecular weight polyethylene or acetal copolymers.

The femoral component may be modified as described in my British Patent Application No. 9310193.9, which describes a knee prosthesis in which the femoral component has a high degree of conformity with the meniscal component.

I claim:

1. A knee prosthesis which comprises:
   (a) a femoral component having a pair of condylar bearing surfaces;
   (b) a tibial component comprising a tibial platform having medial and lateral sides;
   (c) a single unitary meniscal component located between the femoral and tibial components, said single unitary meniscal component having concave areas on medial and lateral sides thereof for receiving the condylar surfaces and being arranged for sliding movement in a generally anterior-posterior (a-p) direction on said tibial platform;
   (d) guide means extending generally along an axis in said a-p direction for guiding said single unitary meniscal component for sliding motion relative to the tibial platform in said a-p direction but with limited rotational movement; and
   (e) stop means on the tibial platform positioned to limit posterior motion of said single unitary meniscal component on the medial side, so as to cause the meniscal component to pivot about a medially displaced axis, said guide means comprising a guide member which is fixed to or is integral with the tibial base plate and engages in a recess in the meniscal component, the meniscal component being rotatable on the guide member.

2. A prosthesis as claimed in claim 1 wherein the guide means comprises a slot or rail extending substantially in the a-p direction.

3. A prosthesis as claimed in claim 2 wherein the rail is 'T'-shaped in cross-section and engages for sliding motion in a correspondingly shaped slot in the meniscal component so that the meniscal component is restrained from lifting off the tibial platform.

4. A prosthesis as claimed in claim 3 wherein the slot or rail is shaped so as to provide a degree of rotational motion which is restricted to about ±15°.

5. A prosthesis as claimed in claim 3 wherein the meniscal component has a posterior side and an anterior side and said slot in the meniscal component is closed at one end thereof, thereby providing a stop at the anterior or posterior side and limiting sliding motion of the meniscal component in the posterior or anterior direction.

6. A prosthesis as claimed in claim 2 wherein the slot or the rail is shaped so as to provide a degree of rotational motion which is restricted to about ±15°.

7. A prosthesis as claimed in claim 1 wherein the stop means comprises an abutment at the posterior side of the tibial platform and medially of said axis.

8. A prosthesis as claimed in claim 7 wherein the abutment is upstanding from the platform.

9. A prosthesis as claimed in claim 1 wherein the guide means comprises a guide rail extending along said axis and having trapping means for restraining undesirable lifting off of the meniscal component.

10. A prosthesis as claimed in claim 9 wherein the guide rail is upstanding from the tibial platform and engages in a slot in the meniscal component.

11. A prosthesis as claimed in claim 9 wherein the guide rail is 'T'-shaped in cross-section.

12. A prosthesis as claimed in claim 1 wherein the guide means comprises a stud engaged in a slot in the meniscal component.

13. A prothesis as claimed in claim 12 wherein stud comprises an upstanding post having a cap which received for relative sliding movement in a slot in the meniscal component.

14. A prosthesis as claimed in claim 12 wherein the slot is a blind slot which is open posteriorly.

15. A prosthesis as claimed in claim 12 wherein the slot is a blind slot wherein is open anteriorly.

16. A prosthesis as claimed in claim 1 wherein the guide means comprises a stud engaged in a slot in the meniscal component.

17. A prosthesis as claimed in claim 16 wherein the stud comprises an upstanding post having a cap which is received in said slot for relative sliding motion in the slot.

18. A prosthesis as claimed in claim 17 wherein the slot is a blind slot which is open posteriorly.

* * * * *